US011154251B2

(12) United States Patent
Genov et al.

(10) Patent No.: US 11,154,251 B2
(45) Date of Patent: Oct. 26, 2021

(54) SYSTEM AND METHOD FOR CLASSIFYING TIME SERIES DATA FOR STATE IDENTIFICATION

(71) Applicant: THE GOVERNING COUNCIL OF THE UNIVERSITY OF TORONTO, Toronto (CA)

(72) Inventors: Roman Genov, Toronto (CA); Gerard O'Leary, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 413 days.

(21) Appl. No.: 16/214,374

(22) Filed: Dec. 10, 2018

(65) Prior Publication Data

US 2019/0246989 A1 Aug. 15, 2019

Related U.S. Application Data

(60) Provisional application No. 62/629,001, filed on Feb. 10, 2018.

(51) Int. Cl.
*A61B 5/00* (2006.01)
*A61B 5/0476* (2006.01)
(Continued)

(52) U.S. Cl.
CPC ............ *A61B 5/7267* (2013.01); *A61B 5/316* (2021.01); *A61B 5/369* (2021.01); *A61B 5/686* (2013.01);
(Continued)

(58) Field of Classification Search
CPC ...... G06N 3/0454; G06N 20/10; G06N 20/00; G06N 20/20; A61L 35/4094; G16H 50/70
See application file for complete search history.

(56) References Cited

U.S. PATENT DOCUMENTS 5,068,818 A 11/1991 Uramoto et al.
6,604,072 B2 8/2003 Pitman et al.
(Continued)

FOREIGN PATENT DOCUMENTS

EP 0624866 B1 7/1999
EP 0936575 B1 7/2004
(Continued)

OTHER PUBLICATIONS

K. H. Lee and N. Verma, "A Low-Power Processor With Configurable Embedded Machine-Learning Accelerators for High-Order and Adaptive Analysis of Medical-Sensor Signals," IEEE Journal of Solid-State Circuits, vol. 48, No. 7, pp. 1625-1637, Jul. 2013.
(Continued)

*Primary Examiner* — Christine H Matthews
*Assistant Examiner* — Joshua Daryl D Lannu
(74) *Attorney, Agent, or Firm* — Bhole IP Law; Anil Bhole; Marc Lampert

(57) ABSTRACT

There is provided a system and method for classifying time series data for state identification. The method including: training a machine learning model to classify occurrences of the state; receiving a new time series data stream; determining whether a current sample in the new time series data stream is an occurrence of the state by determining a classified feature vector, the classified feature vector determined by passing the current sample and samples in at least one continuous sampling window into the trained machine learning model, each continuous sampling window including a plurality of preceding samples from the time series data, an epoch for each respective continuous sampling window determined according to a respective exponential decay rate; and outputting the determination of whether the current sample is an occurrence of the state.

18 Claims, 11 Drawing Sheets

(51) Int. Cl.
    *G06N 20/00* (2019.01)
    *A61B 5/316* (2021.01)
    *A61B 5/369* (2021.01)
    *G06N 20/20* (2019.01)
    *G06N 20/10* (2019.01)

(52) U.S. Cl.
    CPC .......... *A61B 5/7246* (2013.01); *A61B 5/7275* (2013.01); *A61B 5/7282* (2013.01); *G06N 20/00* (2019.01); *G06N 20/10* (2019.01); *G06N 20/20* (2019.01); *A61B 5/4094* (2013.01)

(56) References Cited

U.S. PATENT DOCUMENTS

| | | |
|---|---|---|
| 6,810,285 B2 | 10/2004 | Pless et al. |
| 6,928,398 B1 | 8/2005 | Fang et al. |
| 8,311,821 B2 | 11/2012 | Breebaart et al. |
| 9,691,034 B2 | 6/2017 | Lee et al. |
| 2005/0234309 A1 | 10/2005 | Klapper |
| 2010/0280336 A1* | 11/2010 | Giftakis ............... A61B 5/4803 600/301 |
| 2016/0099010 A1 | 4/2016 | Sainath et al. |
| 2016/0249846 A1 | 9/2016 | Yoo et al. |
| 2017/0232258 A1 | 8/2017 | Trier et al. |

FOREIGN PATENT DOCUMENTS

| | | | |
|---|---|---|---|
| EP | 2429643 A1 * | 3/2012 | ............ G06N 20/00 |
| EP | 2429643 A1 | 3/2012 | |
| EP | 2508225 A1 | 10/2012 | |
| WO | 2000010455 A1 | 3/2000 | |
| WO | 2016193979 A1 | 12/2016 | |
| WO | 2018014127 A1 | 1/2018 | |

OTHER PUBLICATIONS

H. Ismail Fawaz, G. Forestier, J. Weber, L. Idoumghar, and P.-A. Muller, "Deep learning for time series classification: a review," Data Min Knowl Disc, vol. 33, No. 4, pp. 917-963, Jul. 2019.

Z. Cui, W. Chen, and Y. Chen, "Multi-Scale Convolutional Neural Networks for Time Series Classification," Mar. 2016.

H. A. Dau, D. F. Silva, F. Petitjean, G. Forestier, A. Bagnall, and E. Keogh, "Judicious setting of Dynamic Time Warping's window width allows more accurate classification of time series," in 2017 IEEE International Conference on Big Data (Big Data), 2017, pp. 917-922.

H. Deng, G. Runger, E. Tuv, and M. Vladimir, "A Time Series Forest for Classification and Feature Extraction," arXiv:1302.2277 [cs], Feb. 2013.

S. Hochreiter and J. Schmidhuber, "Long Short-term Memory," Neural computation, vol. 9, pp. 1735-1780, Dec. 1997.

C. Gallicchio and A. Micheli, "Deep Echo State Network (DeepESN): A Brief Survey," Dec. 2017.

P. Davis, C. D. Creusere, and W. Tang, "Window length effect on cross frequency coupling in an EEG processing circuit," in 2015 IEEE 58th International Midwest Symposium on Circuits and Systems (MWSCAS), 2015, pp. 1-4.

M. A. B. Altaf, C. Zhang, and J. Yoo, "A 16-Channel Patient-Specific Seizure Onset and Termination Detection SoC With Impedance-Adaptive Transcranial Electrical Stimulator," IEEE Journal of Solid-State Circuits, vol. 50, No. 11, pp. 2728-2740, Nov. 2015.

A. H. Shoeb, "Application of machine learning to epileptic seizure onset detection and treatment," Thesis, Massachusetts Institute of Technology, 2009.

A. Bifet, B. Pfahringer, J. Read, and G. Holmes, "Efficient data stream classification via probabilistic adaptive windows," in Proceedings of the 28th Annual ACM Symposium on Applied Computing—SAC '13, Coimbra, Portugal, 2013, p. 801.

A. Bagnall, J. Lines, A. Bostrom, J. Large, and E. Keogh, "The great time series classification bake off: a review and experimental evaluation of recent algorithmic advances," Data Min Knowl Disc, vol. 31, No. 3, pp. 606-660, May 2017.

L. Ye and Keogh, "Time series shapelets: a new primitive for data mining," in Proceedings of the 15th ACM SIGKDD International conference on Knowledge discovery and data mining—KDD '09, Pads, France, 2009, p. 947.

P. Geurts, "Pattern Extraction for Time Series Classification," in Principles of Data Mining and Knowledge Discovery, 2001, pp. 115-127.

J. L. Elman, "Finding Structure in Time," Cognitive Science, vol. 14, No. 2, pp. 179-211, 1990.

A. J. Lawrance and P. A. W. Lewis, "A new autoregressive time series model in exponential variables (Near(1))," p. 43, Advances in Applied Probability, vol. 13, No. 4 (Dec. 1981), pp. 826-845.

Thabet, Hajer and Ayadi, Mounir and Rotella, Frederic. Sliding window identification with linear-equality constraints. (2015) In: 2015;IEEE 12th International Multi-Conference on Systems, Signals & Devices (SSD15), Mar. 16, 2015-Mar. 19, 2015 (Madhia, Tunisia).

Noppasit Laotaveerungrueng, A high-voltage, high-current multi-charmel arbitrary waveform generator ASIC for neural interface and MEMS applications, Department of Electrical Engineering and Computer Science, Case Western Reserve University, Jan. 2011 (Jan. 2011).

Gerard O'Leary, David M. Groope, Taufik A. Valiante, Naveen Verma, Roman Genov, NURIP: Neural Interface Processor for Brain-State Classification and Programmable-Waveform Neurostimulation, IEEE Journal of Solid-State Circuits, vol. 53, No. 11, Nov. 2018.

Gerard O'Leary1, M. Reza Pazhouhandeh1, Michael Chang1,David Groppe2, Taufik A. Valiante3, Naveen Verma4, Roman Genov1, A Recursive-Memory Brain-State Classifier with 32-Channel Track-and-Zoom $\Delta 2\Sigma$ ADCs and Charge-Balanced Programmable Waveform Neurostimulators, ISSCC 2018 / Session 17 / Technologies for Health and Society / 17.9.

International Search Report and Written Opinion, PCT/CA2019/050172, dated May 22, 2019.

* cited by examiner

SYSTEM AND METHOD FOR CLASSIFYING TIME SERIES DATA FOR STATE IDENTIFICATION

TECHNICAL FIELD

The following relates, generally, to signal processing; and more particularly, to a system and method for classifying time series data for state identification.

BACKGROUND

In various applications, small footprint and/or compact computing systems, such as embedded systems, may be required to record data in a low power manner. An example of this type of requirement on such a system is with an implantable medical device, such as an implantable neural device or implantable cardiac pacemaker. In the case of the implantable neural device, such devices are often tasked with finding brain states through a process that relies on understanding long-term trends in data. However, storing long-term data typically requires a relatively large memory, so some devices are typically limited to storing approximately less than 10 seconds of data. In some devices, recorded neural signals are stored in memory, then typically the data is windowed into time epochs. Windows are then compared to find increases or decreases in the signal. However, window-based approaches are typically limited by the relatively small capacity memory, and as such, typically can lose long-term signal characteristics.

SUMMARY

In an aspect, there is provided a computer-implemented method for classifying time series data for state identification, the time series data comprising a series of samples, the method comprising: training a machine learning model to classify occurrences of the state by classifying a representative feature vector, using a respective training set, the respective training set comprising feature vectors of the time series data labelled with occurrences of the state; receiving a new time series data stream; determining whether a current sample in the new time series data stream is an occurrence of the state by determining a classified feature vector, the classified feature vector determined by passing the current sample and samples in at least one continuous sampling window into the trained machine learning model, each continuous sampling window comprising one or more preceding samples from the time series data, an epoch for each respective continuous sampling window determined according to a respective exponential decay rate; and outputting the determination of whether the current sample is an occurrence of the state.

In a particular case, each continuous sampling window is recursively defined based on the epoch of a previous iteration of the respective window subtracted by the respective decay rate multiplied by the epoch of such previous iteration.

In another case, the at least one continuous sampling window comprises at least two continuous sampling windows, the epoch of each of the continuous sampling windows are defined by a different exponential decay rate.

In yet another case, each exponential decay rate is a reciprocal of a power of 2.

In yet another case, each exponential decay rate is in the range of ½ to $1/(2^{16})$.

In yet another case, each epoch is on the order of minutes or less.

In yet another case, the state vector machine learning model uses one of linear, polynomial and radial-basis function (RBF) kernels.

In yet another case, the at least one continuous sampling window comprises a plurality of continuous sampling windows organized into at least two banks of continuous sampling windows, each bank comprising at least one continuous sampling window, the continuous sampling windows in each bank having a different exponential decay rate than the continuous sampling windows in the other banks.

In yet another case, the time series data comprises physiological signals and the state comprises a physiological event.

In yet another case, the time series data comprises electroencephalography (EEG) signals and the state comprises one or more onset biomarkers associated with a seizure.

In another aspect, there is provided a system for classifying time series data for state identification, the system comprising one or more processors and one or more memory units, the one or more memory units storing the time series data comprising a series of samples, the one or more processors in communication with the one or more memory units and configured to execute: a training module for training a machine learning model to classify occurrences of the state by classifying a representative feature vector, using a respective training set, the respective training set comprising feature vectors of the time series data labelled with occurrences of the state; an input module for receiving a new time series data stream comprising a plurality of samples; an exponential decay module for defining at least one continuous sampling window, each continuous sampling window comprising one or more samples from the time series data preceding a current sample, an epoch for each respective continuous sampling window determined according to a respective exponential decay rate; a support vector module for determining whether a current sample in the new time series data stream is an occurrence of the state by determining a classified feature vector, the classified feature vector determined by passing the current sample and samples in the at least one continuous sampling window into the trained machine learning model; and an output module for outputting the determination of whether the current sample is an occurrence of the state.

In a particular case, each continuous sampling window is recursively defined based on the epoch of a previous iteration of the respective window subtracted by the respective decay rate multiplied by the epoch of such previous iteration.

In another case, the at least one continuous sampling window comprises at least two continuous sampling windows, the epoch of each of the continuous sampling windows are defined by a different exponential decay rate.

In yet another case, each exponential decay rate is a reciprocal of a power of 2.

In yet another case, each exponential decay rate is in the range of ½ to $1/(2^{16})$.

In yet another case, each epoch is on the order of minutes or less.

In yet another case, the state vector machine learning model uses one of linear, polynomial and radial-basis function (RBF) kernels.

In yet another case, the exponential decay module defines a plurality of continuous sampling windows organized into at least two banks of continuous sampling windows, each bank comprising at least one continuous sampling window, the continuous sampling windows in each bank having a different exponential decay rate than the continuous sampling windows in the other banks.

In yet another case, the time series data comprises physiological signals and the state comprises a physiological event.

In yet another case, the time series data comprises electroencephalography (EEG) signals captured by electrodes in communication with the system, and the state comprises one or more onset biomarkers associated with a seizure.

These and other aspects are contemplated and described herein. It will be appreciated that the foregoing summary sets out representative aspects of the system and method to assist skilled readers in understanding the following detailed description.

DESCRIPTION OF THE DRAWINGS

A greater understanding of the embodiments will be had with reference to the Figures, in which.

DETAILED DESCRIPTION

Figure 1:
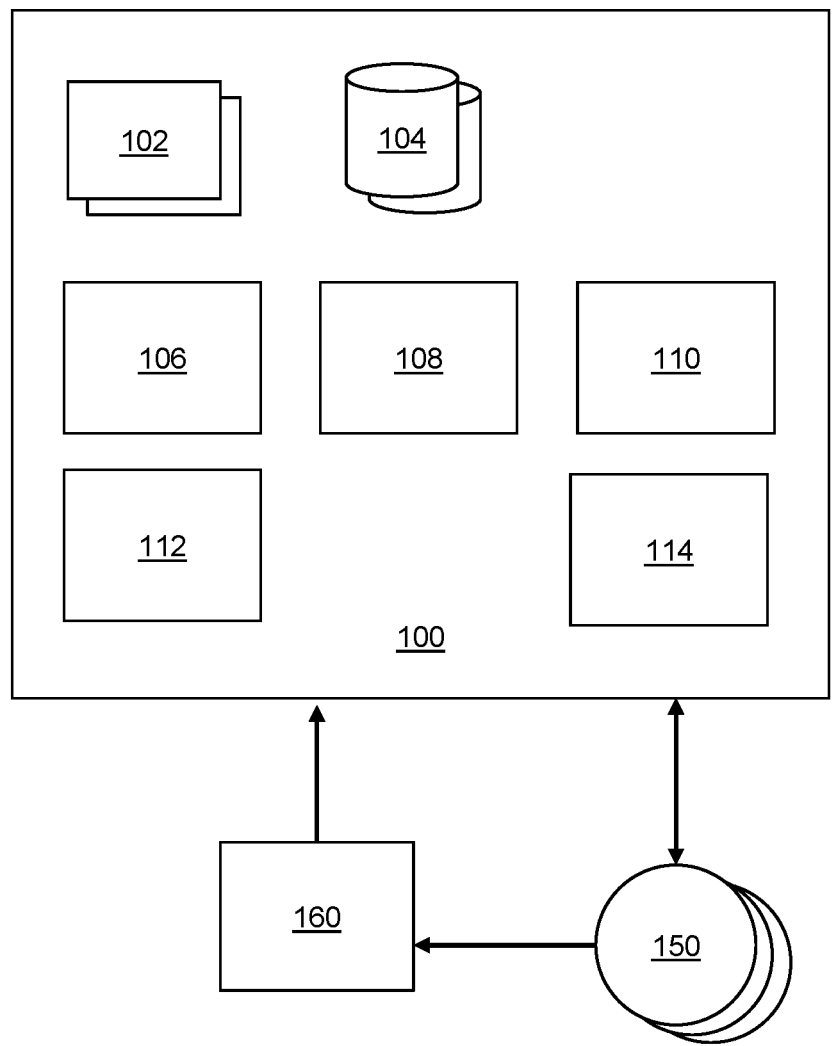
FIG. 1 shows a block diagram of an embodiment of a system for classifying time series data for state identification, according to an embodiment.

For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practised without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender. Further definitions for terms may be set out herein; these may apply to prior and subsequent instances of those terms, as will be understood from a reading of the present description.

Any module, unit, component, server, computer, terminal or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

Embodiments described herein generally provide a system and method for neural interfacing.

Applicant has determined that various advantages may be achieved with the embodiments described herein using an array of hardware approximators for moving average filters, where portions of new data are incorporated into a single register, and previous values decay exponentially. In this way, advantageously, trends in neural signals ranging from years to seconds can be stored on an implanted device without requiring large and power-inefficient electronic memory. The embodiments described herein are intended to allow for various advantages; for example, reducing the size and cost of implantable brain state classifiers, reducing power requirements for devices, enabling implicit storage of long-term data with low footprint, and enabling more accurate and efficient time series classification. With respect to implantable neural devices, the embodiments described herein are intended to enable higher performance brain state classification with fewer false positives and more true positives, and allow implicit storage of long-term data without the need for large, expensive, and power inefficient memories.

While the following embodiments may refer to implantable neural devices in applications for seizure neuromodulation, it will be appreciated that the exponentially decaying memory (EDM) techniques described herein can be used in various suitable computing devices, for example, other implantable medical devices. Generally, the embodiments described herein relate to the classification of time series data for state identification; for example, seizures in epilepsy, tremors in Parkinson's disease, neurological artefacts due to Alzheimer's disease, or the like. It is appreciated that the embodiments described herein with respect to classifying time series data can be applied to any suitable field involving time-series classification; for example, voice recognition, financial data analysis, or the like.

Distinguishing seizure activity from normal brain activity can be a difficult task because of potentially great variation in seizure morphology. As described herein, machine learning enables the utilization of large volumes of patient recordings to accurately distinguish pathological from physiological activity. Thus, allowing for responsive closed-loop neuromodulation which can proactively detect and inhibit the onset of seizures. In such an approach, supervised learning models can be utilized to maintain low false-detection rates for improved power efficiency and reduced side-effects. However, the use of supervised learning classifiers for seizure detection can expose a class imbalance problem which arises from a lack of ictal recordings compared to large volumes of inter-ictal data. Furthermore, supervised classification systems, in some cases, can require accurate data labeling, and can be vulnerable to the human error in annotating complex EEG recordings.

The somewhat limited success in the pharmacologic treatment of epileptic syndromes has aroused an increasing interest in the possibility of stopping seizures with brief direct electrical intracerebral stimulation. Support for the possible success of electrical perturbations in preventing seizures is based on the assumption that if the dynamics of the abnormal synchrony that characterizes paroxysms is perturbed by stimulations, then the ictus may not appear, or will be forced to stop if already initiated. Thus, the implementation of "minimal" (short duration, low frequencies and intensities) perturbations to stop the transition from the preictal activity to the ictal, convulsive event by a precisely timed brief stimulation is a highly beneficial solution. Contrary to the current deep brain or vagus nerve stimulation paradigms that use intermittent (continuous) stimulation, present embodiments stimulate when a paroxysm is about to occur, using an on-demand feedback stimulation method based on real-time analysis of brain signals that detects a precursor of paroxysms, and implements a brief (e.g., 5 second) stimuli to stop the transition to the ictal event. Generally, an abnormal oscillation originates from an epileptogenic zone (often in hippocampus in temporal lobe epilepsy), which may disrupt theta wave (and others) synchronization with the other hippocampus. Over time, this focal oscillation spreads and often propagates contralaterally and develops a paroxysmal discharge. A feedback stimulator could disrupt the local epileptic oscillation and abort the seizure development.

The following terminology is used in the present disclosure. "Paroxysms" are any abnormal electrographic activities (e.g., having a duration of greater than or equal to 10 seconds) associated with relatively high frequency and amplitude of spikes. When no apparent behavioral alterations are observed at the time of an electrographic paroxysm, the term "nonconvulsive paroxysm" is used, whereas the expression "convulsive paroxysm" is used if an abnormal behavior is observed concomitant with abnormal electrographic recording. The "paroxysm onset" is defined as the time when the amplitude of the electrographic recording in the paroxysm becomes greater than twice the standard deviation of the baseline activity. The "early paroxysm detection time" is the time between the detection of the seizure precursor and the paroxysm onset. The "preictal period" is defined as 1 minute before the paroxysm onset, and the "interictal period" is the time between the end of one paroxysm and the preictal of the next. The convulsive paroxysms are defined according to the Racine scale (class III to class IV), whereas the nonconvulsive paroxysms are class I or class II seizures.

Activity in EEG signal frequency bands can be used to categorize irregular neural recordings. Such events include electrographic seizure onsets and interictal discharges (IIDs). This assessment is generally based on temporo-spectral changes such as low-voltage fast activity in intracranial electroencephalogram (iEEG) seizure onset. In the present embodiments, in order to provide a technological solution to capture such changes, Exponentially Decaying Memory (EDM) is presented as a hardware efficient mechanism to represent temporal feature characteristics for machine learning. In an embodiment described herein, an unsupervised learning based One-class Support Vector Machine (OC-SVM) can be used. This approach can navigate the technical problems related to class imbalance and data labeling by, for example, learning to distinguish normal neural activity from segments of clinical interest. In a particular case, irregular recording periods indicated by the OC-SVM can be reviewed by a user, such as an epileptologist, enabling ictal data to be labelled and accumulated over time. With increasing volumes of data, specialized supervised learning classifiers can be trained more effectively for closed-loop applications.

Generally, chronic neural recording implants experience considerable signal variability over time, leading to a gradual degradation of classifier performance. Thus, continuous model re-training is generally necessary to adapt to changing physiological recording conditions and maximize the treatment efficacy. However, this can be impractical to perform on an implantable device as power-consumption is a primary consideration to reduce both heat dissipation and the risks associated with battery replacement surgery. In an embodiment, there is provided a patient-localized microserver that can communicate with an implanted device to enable incremental training. In some cases, data recorded by the device can be sent to the server and processed by an FPGA-accelerated OC-SVM. iEEG segments which are considered irregular are archived and sent to a remote epileptologist for review. Once an assessment is made, the microserver can re-train the model to be uploaded to the implanted device.

Figure 9:
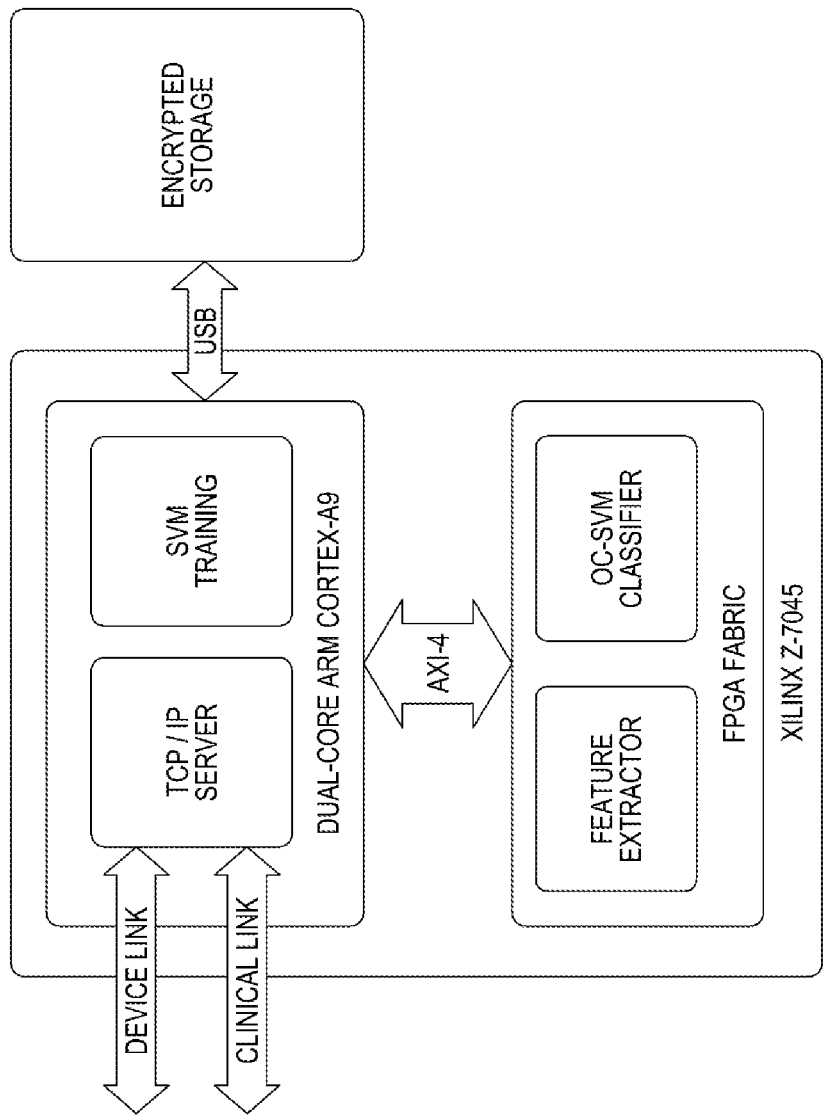
FIG. 9 shows an example microserver system using the system of FIG. 1.

In a diagrammatic example illustrated in FIG. 9, an example system is shown implemented using a Xilinx Zynq SoC. In this example, a dedicated dual-core CPU hosts an on-chip Linux operating system (OS) which runs in parallel with the FPGA fabric. SVM training can be performed on the microserver with encrypted patient data maintained on USB storage. A TCP/IP implementation allows data to be streamed wirelessly from a compatible neuromodulation device. To reduce the implanted device's power requirements for data transmission, raw samples can be sent rather than higher dimensional features. In most cases, this requires feature extraction to be replicated on the microserver. Communication with a remote EEG analyst is supported via, for example, an ethernet network interface. In an example, feature extraction and machine learning accelerators can be implemented on the FPGA fabric.

To detect anomalous activity in neural signals, spectral energy in physiological signal bands can be used to label electrographic events. Signal bands of interest can be extracted by passing recorded samples through parallel bandpass filters for, for example, Delta (<4 Hz), Theta (4-8

Hz), Alpha (8-13 Hz), Beta (13-30 Hz) and Gamma (30-60 Hz) bands. In this example, a 256-tap Type-1 FIR filter can be used for each band with a symmetric impulse response, allowing coefficient multiplications to be shared. Each iEEG channel can be processed sequentially and filter states are stored in block RAM (BRAM) between sample processing. For each band, the absolute value of each output sample can be taken as a measure of signal energy. This approximation of instantaneous energy can be accumulated over a time window to generate a temporo-spectral measure of the signal.

To capture temporal evolution of machine learning features, such as signal energy, some approaches use a windowing approach where contiguous time epochs are concatenated to form a feature vector to be classified. Using this approach, it is possible to learn temporal differences between windows for events such as seizure onset. However, window-based approaches have several limitations in performance and hardware efficiency. As an example, processing larger windows requires proportionally large accumulation logic. In another example, if classification is performed at every epoch, test vector re-ordering logic may be necessary to remove old windows and add new windows. In another example, a minimum detection latency is the time required to generate a window (typically multiple seconds). In another example, as EEG recordings are patient specific, one window size may give sufficient temporal resolution in one case, but may not be optimal for another. In contrast, embodiments of the present invention advantageously provide the ability to learn feature timescales in a patient-specific manner to maximize classification performance; for example, using Exponentially Decaying Memory (EDM) as described herein.

A support vector machine (SVM) can be used as a supervised learning model for classification tasks of two or more classes. Generally, a similar number of examples in each class is required to prevent classifier bias. In the case of seizure detection, ictal activity is rare and accurate classification is generally a necessity to prevent the onset of a seizure.

The one-class SVM, described herein, provides an approach for datasets with class imbalances. It can be viewed as a regular two-class SVM, where the training data is taken as one class, and the origin is taken as the only member of the second class. Training is performed without labels, where data is mapped to a kernel space and separated from the origin by a hyperplane with maximum margin. To classify an input feature vector, a decision function is evaluated to distinguish an inlier (f(x)>0), from an outlier (f(x)<0):

$$f(x) = \text{sgn}\left(\sum_{i=1}^{N} a_i K(\vec{sv}_i, \vec{x}) - b\right)$$

Where $sv_i$ are the support vectors used to construct the hyperplane, $a_i$ are the corresponding weights, b is the classifier bias term, and K is implemented here as a Radial Basis Function (RBF) kernel, defined as:

$$K(\vec{x}, \vec{sv}) = e^{-\gamma \|\vec{sv} - \vec{x}\|_2}$$

Figure 10:
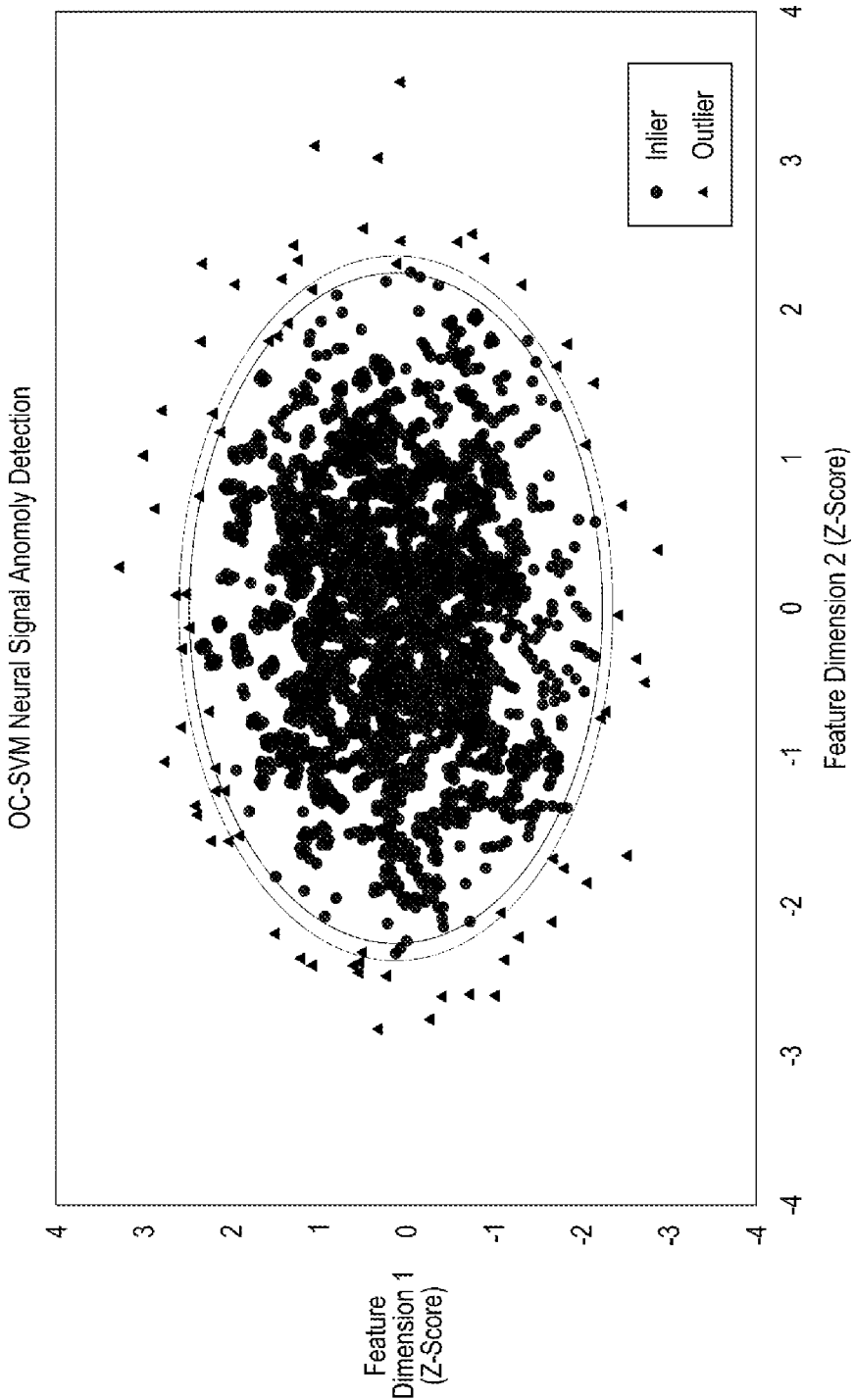
FIG. 10 shows an exemplary experiment for detecting seizures using the system of FIG. 1.

This concept is exemplified in FIG. 10, where a model is trained using normal physiological activity (circles). The extracted test vectors classified as outliers (triangles) could indicate anomalous activity such as inter-ictal discharges (IIDs) or subclinical seizures.

In order to effectively use closed-loop neuromodulation for treating neurological disorders, (1) analog circuits are generally needed to monitor brain activity uninterruptedly even during neurostimulation, (2) energy-efficient high-efficacy processors are generally needed for responsive, adaptive, personalized neurostimulation, and (3) safe neurostimulation paradigms with rich spatio-temporal stimuli are generally needed for controlling the brain's complex dynamics. In embodiments described herein, an implantable neural interface processor (NURIP) is provided that generally includes the above advantages, thus generally able to perform brain state classification for reliable seizure prediction and contingent seizure abortion. Thus, able to classify brain states, (for example, seizures in epilepsy or tremors in Parkinson's disease) and provide responsive intervention with electrical stimulation. In other embodiments, NURIP can be used for enhancing other psychological states; for example, memory recall, sleep states, or the like. In an embodiment, NURIP is a low-power complementary metal-oxide silicon (CMOS) device which monitors digitized neural signal recordings and detects pathological states. When a state is detected, the device generates electrical stimulation waveforms to influence neural behaviour and lead the brain to a normal physiological state.

Some devices can use simplistic biomarkers for seizure detection, thus typically requiring manual tuning by clinicians and typically have high noise levels resulting in a high number of false stimulations, increasing side-effects, and decreasing battery life. Some devices can also use manual biomarker thresholding for classification, which also typically requires manual tuning and a high false alarm rate. Some devices can also use basic waveforms that can limit the ability to specifically target stimulation and precisely control neural activity.

Figure 3:
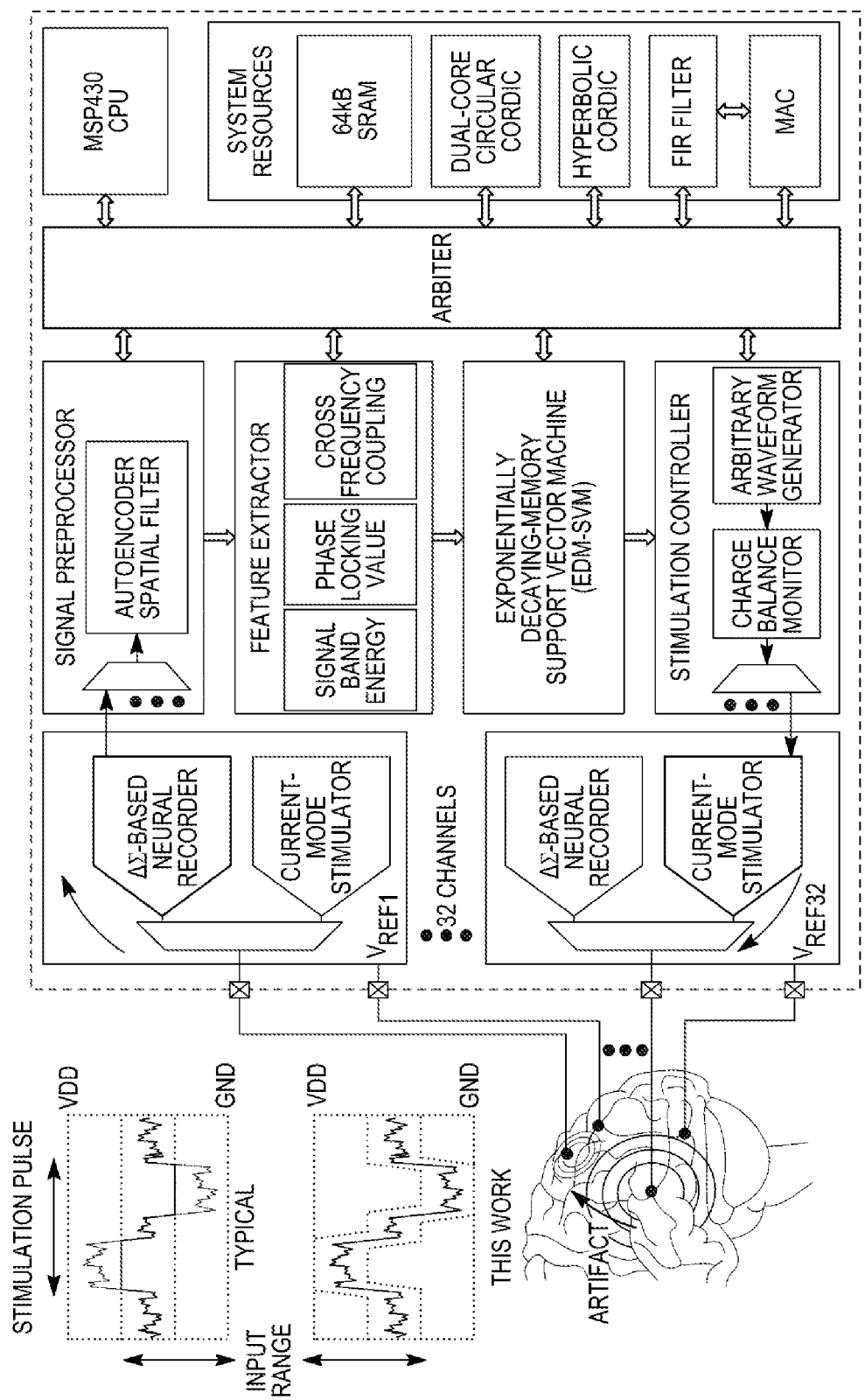
FIG. 3 shows an example system architecture for an implantable neural interface processor (NURIP)

In an example of the NURIP system level architecture, as diagrammatically illustrated in FIG. 3, the NURIP can include 32 bidirectional channels, each with a digitally charge-balanced arbitrary waveform generator (AWG) type neurostimulator and an input-tracking $\Delta^2\Sigma$-based analog-to-digital converter (ADC). The AWG advantageously generates complex neuromodulation waveforms to enhance spatial selectivity and to enable the precise control of neural activity. Thus, advantageously, tissue and device electrode damage is mitigated using a charge accumulation waveform monitor and applying a charge recovery waveform when safe levels are exceeded.

Some stimulation strategies use "low resolution" bi-phasic pulse waveforms to reduce damage caused by charge buildup at brain-electrode interface. Low-resolution, low-selectivity biphasic waveforms are sufficiently different from measured EEG activity. Additionally, low-resolution waveforms limit the ability to selectively target and control neural activity to treat disorder symptoms. In contrast, high resolution waveforms typically enable more intricate interaction with a nervous system but are typically more difficult to regulate from a charge perspective.

In the present embodiments, the AWG advantageously permits on-chip generation of complex waveforms to enhance spatial selectivity and to enable the precise control of neural activity. In this way, the AWG charge accumulation register monitors neural waveform and applies charge recovery waveform when safe levels are exceeded. Advantageously, the AWG can enable more intricate interaction with the nervous system in order to control neurological disorders because charge balancing can ensure compliance with charge limits.

The ADC can be configured to automatically detect any sharp transitions in the intracranial electroencephalogram (iEEG), such as those due to a stimulation artifact. The ADC can also be configured to then shift a high-resolution input range to zoom to the input signal, such as anywhere within the power rails. This approach is advantageous because it generally experiences no blind intervals caused by sharp input transitions. An input digital stage can include an autoencoder neural network for both iEEG spatial filtering and dimensionality reduction. Dedicated feature extraction blocks can be used to implement univariate (signal-band energy (SE)) and multivariate (phase locking value (PLV) and cross frequency coupling (CFC)) neural signal processing. A proceeding support vector machine (SVM) accelerator employs these features for brain state classification. A further processor can be used to facilitate additional custom feature extraction and system control, as suitable. In response to a detection of a pathological brain state, an appropriate modulation waveform is generated to control the operation of the current-mode neurostimulator.

Figure 4:
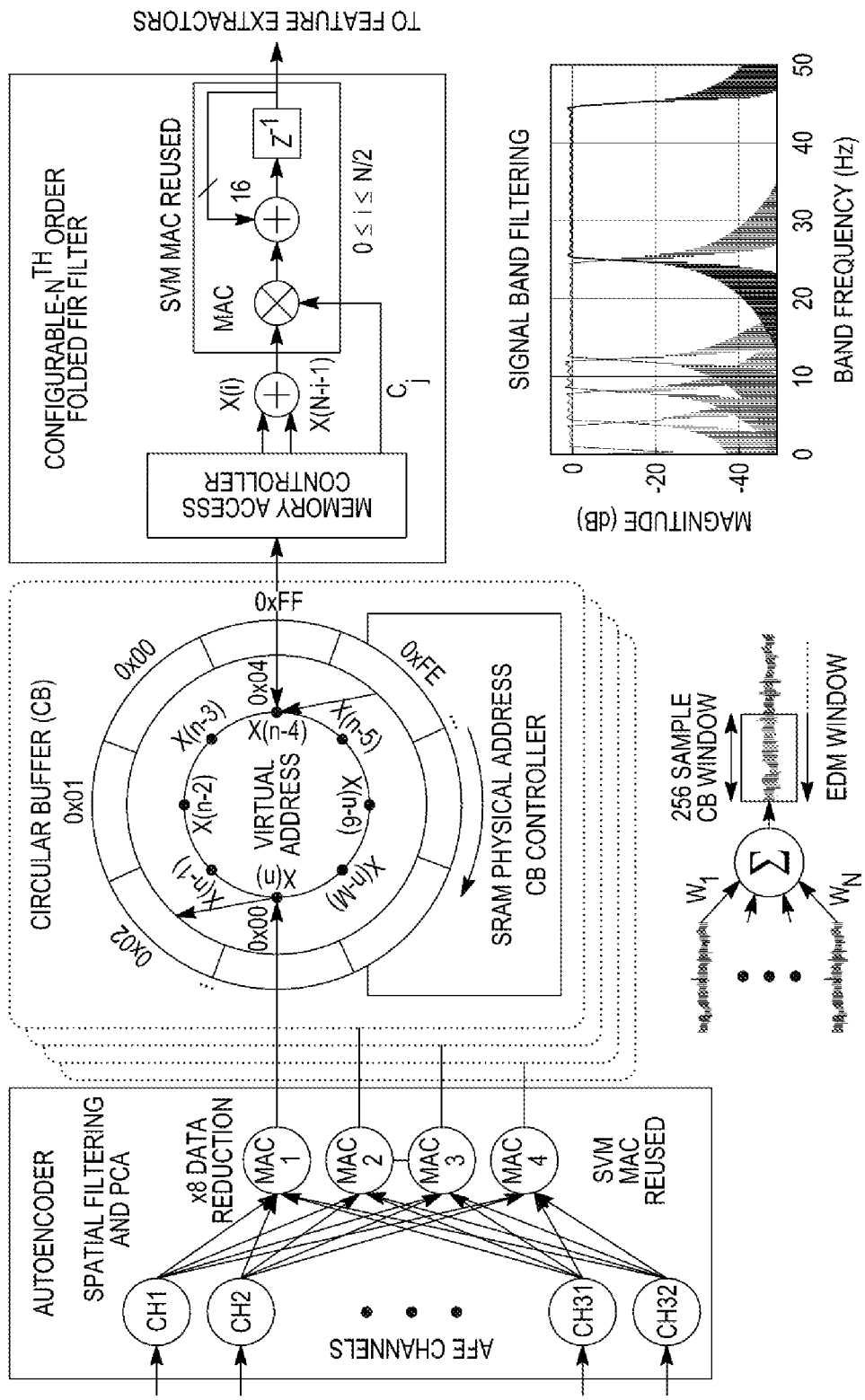
FIG. 4 illustrates an exemplary autoencoder neural network for spatial filtering and finite impulse response (FIR) spectral filtering.

FIG. 4 illustrates an exemplary embodiment of NURIP data management and signal band energy feature extraction, showing both spatial and spectral filtering of the input neural signals. In this embodiment, an auto-encoder neural network is configured to perform spatial filtering and FIR spectral filtering; having a dimensionality reduction from 32 recording channels to 4 weighted combinations, such as in principal component analysis; thus, reducing the processing requirements by approximately eight times. Sixteen hardware-based circular buffers (four are shown) enable processing of neural recording streams, in some cases online, with a 256-sample window. The buffers are mapped to 8 kB of address space within 64 kB of global static RAM (SRAM). Incoming samples are mapped to varying physical addresses whereas the corresponding virtual addresses can be fixed. An output stream can be band-pass filtered using a global configurable FIR filter, which utilizes coefficients symmetry to halve the number of Multiplier Accumulators (MACs).

Figure 5A:
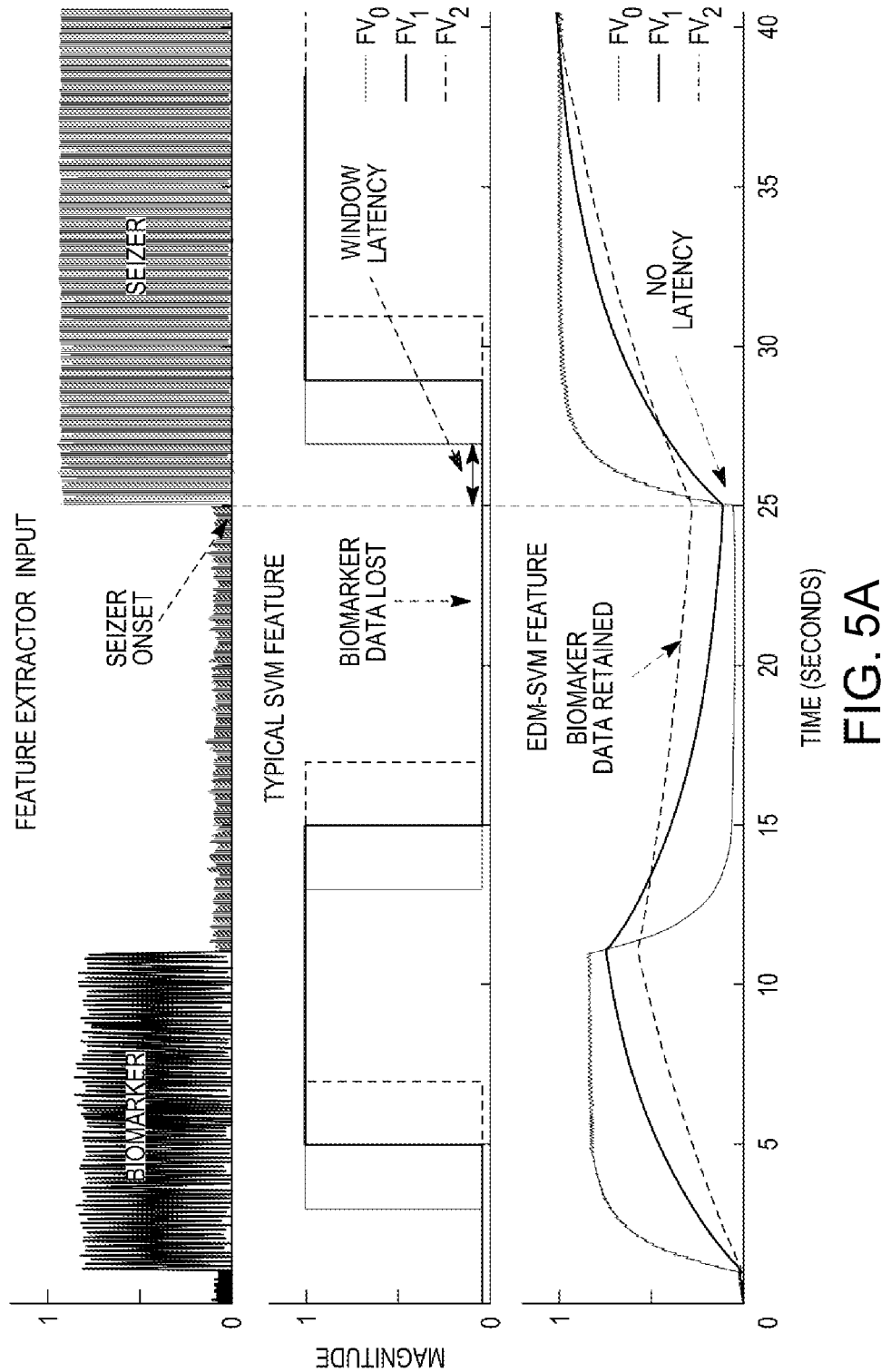
FIG. 5A illustrates an exemplary conventional windows classifier in comparison with an exponentially decaying memory (EDM) classifier.
Figure 5B:
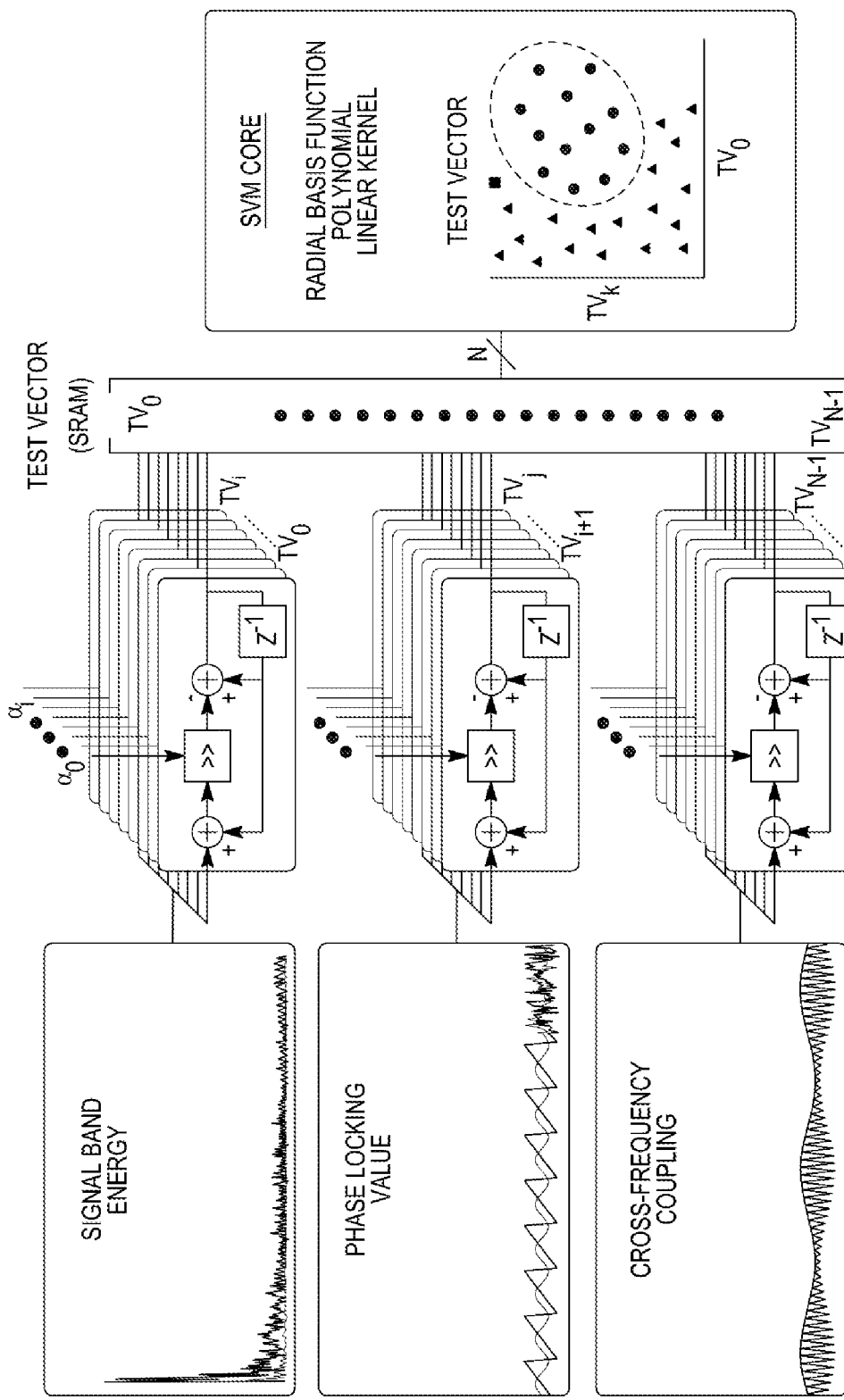
FIG. 5B illustrates an exemplary multi-variate feature extraction array connected to an exponentially decaying memory support vector machine (SVM), which are then connected to an SVM classifier.

In an exemplary embodiment, an array of three configurable neural signal feature extractors, shown in FIG. 5B, can be used to enable custom patient-specific processing to maximize classifier performance. The absolute output value of each bandpass filter is taken as a measure of signal energy. As shown in FIGS. 5A and 5B, a specific power signature in the δ, θ, α, β and γ iEEG bands can be indicative of a seizure. FIG. 5A illustrates a windows classifier in comparison with an EDM classifier. FIG. 5B illustrates a multi-variate feature extraction array (in this case, three biomarker extractors) connected to an exponentially decaying memory support vector machine (an EDM array circuit connected to each of the three biomarkers), which are then connected to an SVM classifier. The phase locking value (PLV) extractor shown in FIG. 5B can be used to detect phase difference precursors of an upcoming seizure onset. An analytic signal can be obtained using a global Hilbert FIR filter along with a dual-core coordinate rotation digital computer (CORDIC) block to extract the phase difference between two input channels. Advantageously, this embodiment has efficient resource reuse to provide an overall footprint reduction of nine times in comparison with other approaches. Cross-frequency coupling (CFC) is a key mechanism in neuronal computation and its abnormal appearance can serve as a key spatial biomarker for seizure detection. Low-frequency brain rhythms modulate high-frequency activity and a resulting envelope can be extracted with re-use of PLV hardware. CFC can then be determined as a synchrony between the extracted envelope and a low-frequency modulating signal. Advantageously, the ensemble of these three biomarkers can yield a uniquely high-dimensional feature space for the classifier.

In the case of seizure prediction, onset biomarkers are subtle and can occur minutes before seizure onset. This presents a challenge in processing and memory requirements for implantable devices. The NURIP includes an exponentially decaying-memory support vector machine (EDM-SVM) accelerator for efficient classification of long-term temporal patterns. The EDM-SVM input stage, shown in FIGS. 5A and 5B, recursively captures a feature's history across multiple timescales, up to multiple minutes, using a combination of memory decay rates to enable the learning of temporal relationships. An efficient implementation using shift and add operations is implemented by constraining decay coefficients to powers-of-two. The SVM accelerator core allows the selection of linear, polynomial and radial-basis function (RBF) kernels to trade off between performance, energy and memory usage. As the EDM is updated, for example at every sample, classification can be performed continuously to minimize detection latency.

To capture temporal evolution of machine learning features such as signal energy, some methods typically use a windowing approach where contiguous time epochs are concatenated to form a feature vector to be classified. Using this approach, it is possible to learn temporal differences between windows for events such as seizure onset. Window-based approaches have several limitations in performance and hardware efficiency. As an example, processing larger windows requires proportionally large accumulation logic. As another example, if classification is performed at every epoch, test vector re-ordering logic may be necessary to remove old windows and add new windows. As another example, a minimum detection latency is typically the time required to generate a window, which is typically multiple seconds. As another example, EEG recordings are typically patient specific, so one window size may give sufficient temporal resolution in one case, but may not be optimal for another. Due to the fact every person or patient is different and presents different neurological biomarkers, advantageously, using machine learning approaches, as embodied herein, allows the system to learn and apply stimulation on a patient-by-patient basis.

Advantageously, some of the present embodiments use feature timescales in a patient-specific manner to maximize classification performance. Exponentially decaying memory (EDM) is an approach which can provide such an advantage. Rather than accumulating and concatenating fixed windows, the system can use a continuous sampling recursive window defined by:

$$\text{EDM}_{(t)} = \text{EDM}_{(t-1)} - \alpha[\text{EDM}_{(t-1)} - x_{(t)}] \quad (1)$$

In the above formula (1), in some cases, an initial EDM "magnitude" can be 0. In this way, a new value for an EDM is the old value, minus a weighted difference between the old value and the new value. The new value, x(t), can be incorporated based on a set learning rate.

In some cases, this approach incorporates new inputs or degrades existing memory of a feature according to a decay rate, α. Where:

$$\alpha = \frac{1}{N}, N = 2^i, 1 < i < 16 \quad (2)$$

Advantageously, EDM can minimize latency as the output is continuous and can be classified at every sample, rather than every window. Furthermore, temporal resolution can be maximized as accumulation over an epoch is not required. EDM can be implemented efficiently in hardware using shift and add operations if N is limited to powers-of-two. This efficiency provides a technological advantage by allowing multiple EDMs to be used in parallel, enabling multiple timescales to be processed simultaneously at a low computational cost.

In the present embodiment, after the signal energy is extracted for a given EEG band, its value is passed to a corresponding bank of one or more EDMs. Each EDM implements a different decay rate, $\alpha$, complementing one another by offering a different temporal perspective of the input feature to be used for classification. In this way, small values of a can result in longer-term memory, while larger values can capture finer time resolutions.

In some cases, different decay rates can be combined by arranging the different decay rates linearly in memory. For example, Decay Rate 1 can be located at memory address 0x0 (element 0 in the test vector), Decay Rate 2 can be located at 0x1 (element 1). During training, the model can be optimized based on an assumption that Decay Rate 1 will be at a first element in a test vector, and the like.

Figure 6:
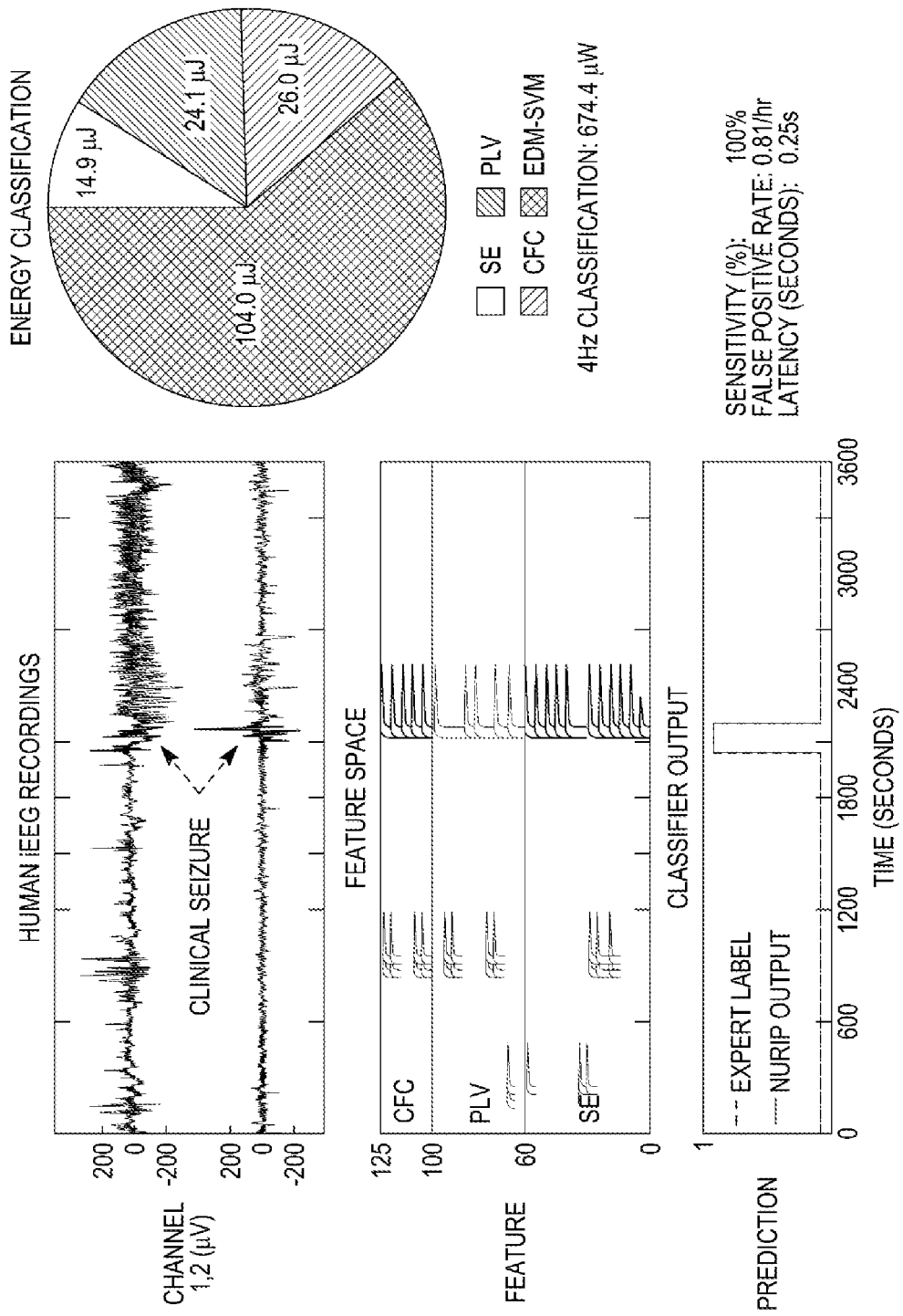
FIG. 6 illustrates an exemplary representation of the performance of NURIP's EDM implementation.
Figure 7:
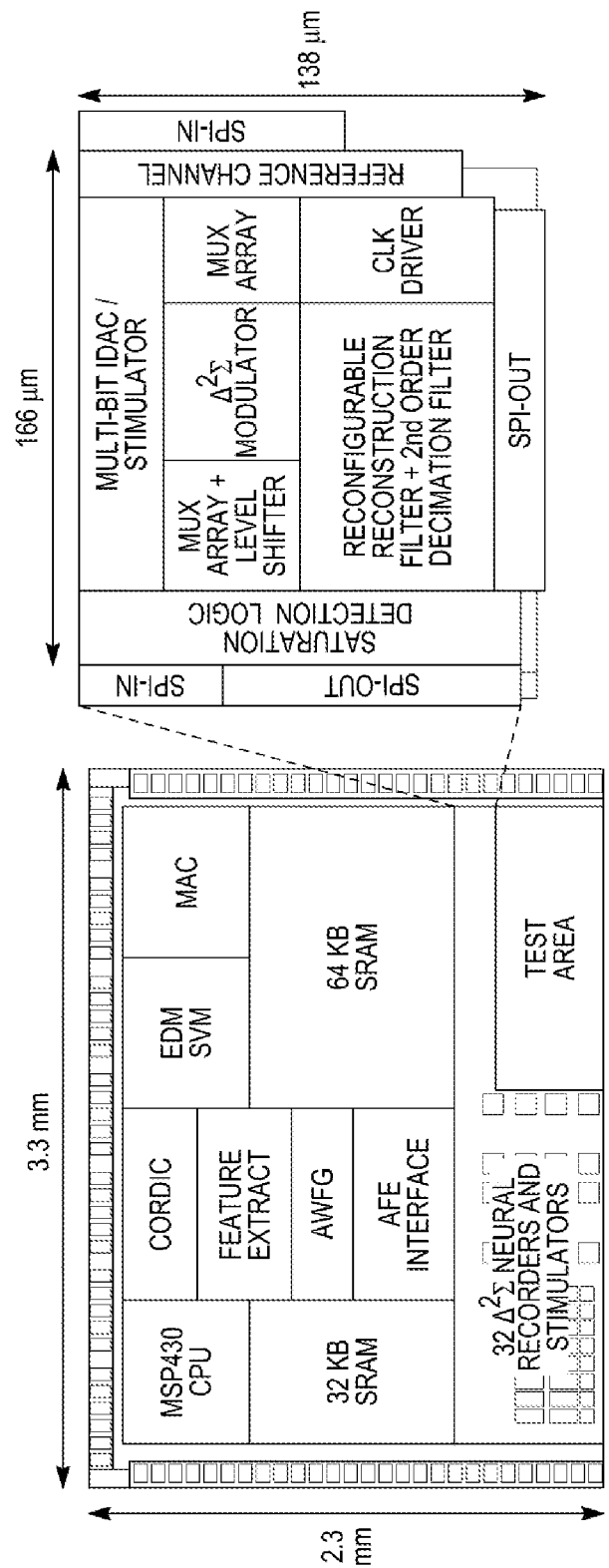
FIG. 7 illustrates an exemplary system on chip (SoC) micrograph.
Figure 8:
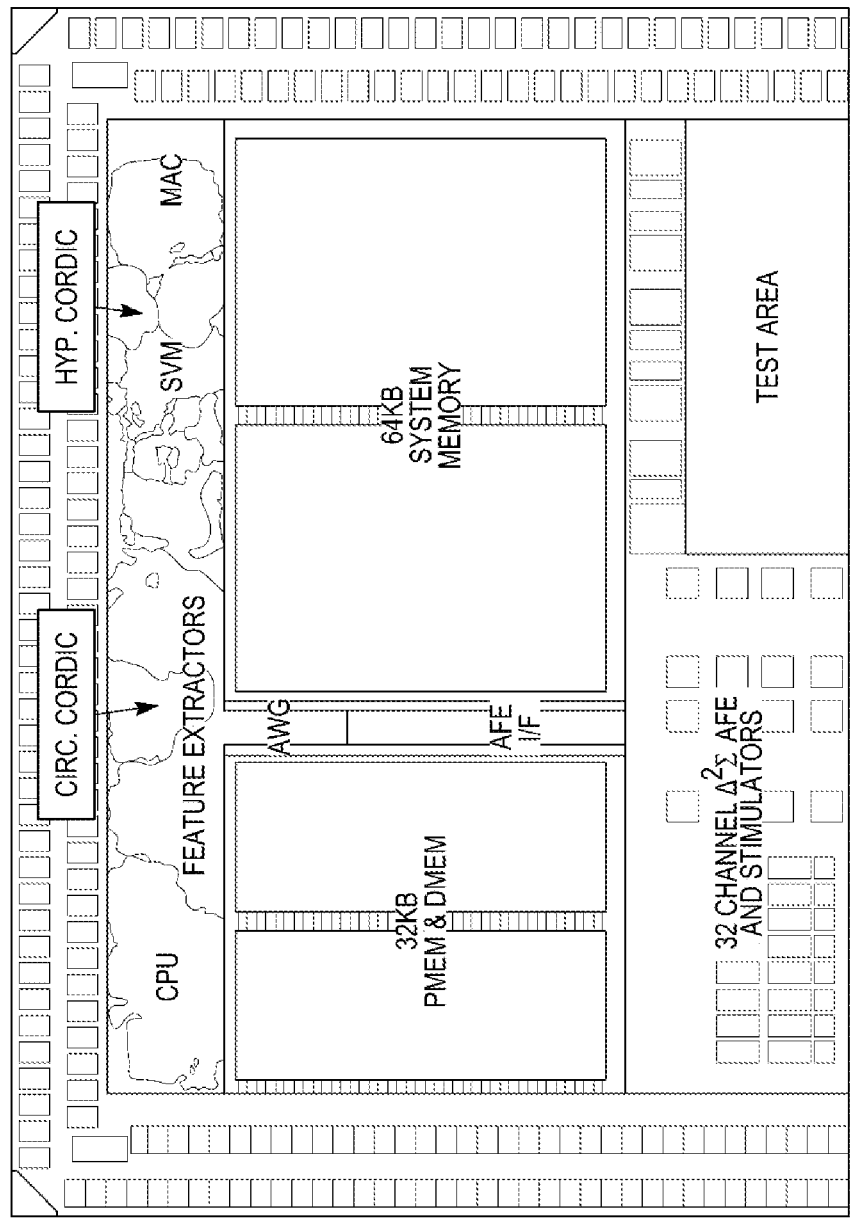
FIG. 8 illustrates another exemplary SoC micrograph.

FIG. 6 illustrates an exemplary representation of the performance of NURIP's EDM implementation on an application specific integrated circuit using an intracranial EEG database. In this example, an extracted feature space used for classification consists of 125 dimensions derived through offline feature selection and is constrained to under 200 support vectors by the on-chip SRAM. Applicant observed a sensitivity of 100% and a false positive rate (FPR) of 0.81 per hour. In this case, it was measured that a classification rate of 4 Hz requires a power consumption of approximately 674.4 W with a nominal voltage of 1.2 V and an operational frequency of 10 MHz. Two examples of a system on chip (SoC) micrograph and the channel floorplan are shown in FIGS. 7 and 8, respectively. The following chart demonstrates exemplary advantages of the NURIP chip of the present embodiment compared with various other devices (chips) both in terms of the channel performance and digital processing performance:

operation of the system 100, the one or more processors 102 can be configured to execute a training module 106, an input module 108, an exponential decay module 110, a support vector module 112, and an output module 114.

In an embodiment, the system 100 is connectable to one or more electrodes 150 implantable in a patient's brain via an analog front-end 160.

Figure 2:
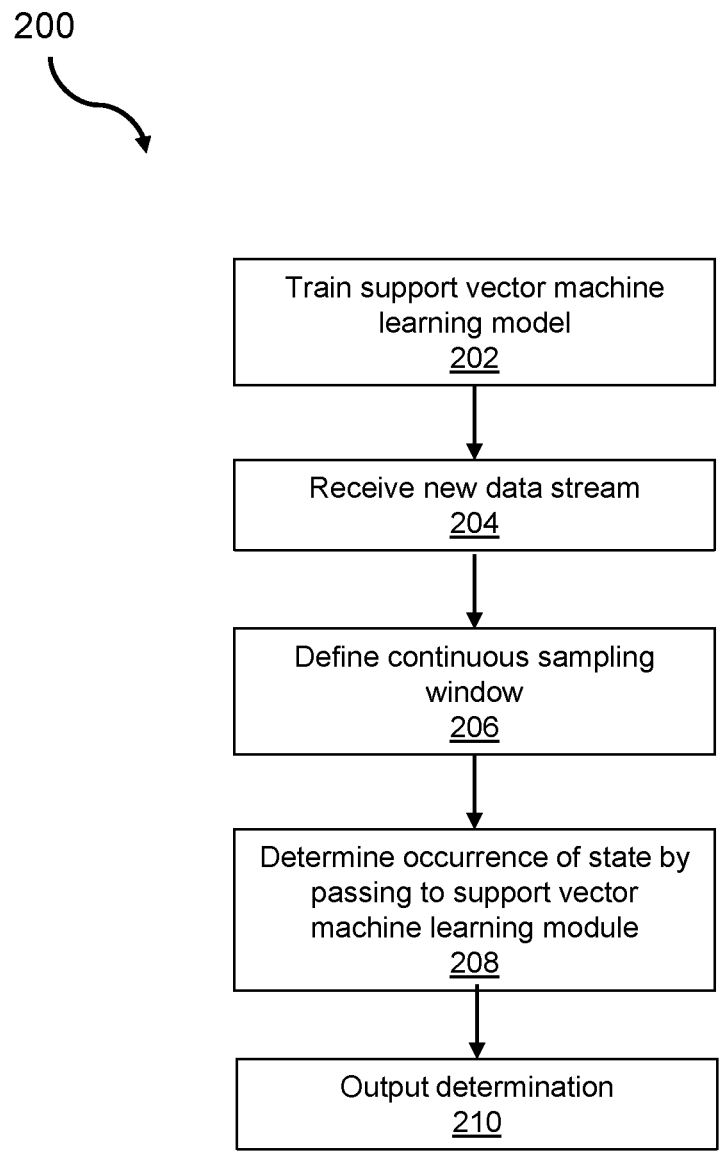
FIG. 2 shows a flowchart for a method for classifying time series data for state identification, according to an embodiment.

Turning to FIG. 2, a computer-implemented method for classifying time series data for state identification 200, according to an embodiment, is shown. At block 202, the training module 106 trains a machine learning model (for example, a support vector machine (SVM)) to classify occurrences of the state by classifying a representative feature vector, using a respective training set. The respective training set comprising feature vectors of the time series data labelled with occurrences of the state.

At block 204, the input module 108 receives a new time series data stream comprising a plurality of samples. In an example, the new time series data can come from data already stored in the one or more memory units. In another example, the new time series data can come from a signal received by the system, for example an EEG signal received from electrodes.

At block 206, the exponential decay module 110 defines at least one continuous sampling window, each continuous sampling window comprising one or more samples from the time series data preceding a current sample. An epoch for each respective continuous sampling window determined according to a respective exponential decay rate.

At block 208, the support vector module 112 determines whether a current sample in the new time series data stream is an occurrence of the state by determining a classified feature vector. The classified feature vector is determined by passing the current sample and samples in the at least one continuous sampling window into the trained machine learning model.

At block 210, the output module 114 outputs the determination of whether the current sample is an occurrence of the state. In an example, the output module 114 can output to a user output device, such as a monitor or speaker. In another example, the output module 114 can output to

|  | Chip #1 | Chip #2 | Chip #3 | Chip #4 | NURIP |
| --- | --- | --- | --- | --- | --- |
| TECHNOLOGY ($\mu$m) | — | 0.18 | 0.18 | 0.13 | 0.13 |
| FEATURE EXTRACTION | CPU | FFT, Entropy | SE | PLV | PLV, CFC, SE, CPU |
| CLASSIFIER | SVM | LLS | $D^2$A-LSVM | Threshold | EDM-SVM |
| SAMPLE MEMORY | 6 s | 96 samples | 3 s | 64 samples | $\infty$ (EDM) |
| LATENCY (s) | 2 | 0.8 | 1 | — | <0.1 |
| MEMORY (kB) | 64 | 0 | 64 | 0 | 96 |
| WAVEFORM GEN. | — | Bi-phasic | Bi-phasic | — | AWG |
| CHARGE BALANCING | — | — | PVTES | — | BECR |
| ENERGY/CLASS. ($\mu$J) | 273 | 77.91 | 2.73 | — | 168.6 |

Turning to FIG. 1, a system for classifying time series data for state identification 100, according to an embodiment, is shown. The system 100 includes one or more processors 102 in communication with one or more memory units 104. The one or more memory units 104 store the operating system and programs, including computer-executable instructions for implementing the system 100. During another computing system, or other module on the current system, via a communication network. In another example, the output module 114 can output to a neurological stimulation device or system, such as a waveform generator as described herein.

In an example of the present embodiments, the present inventors experimentally demonstrated the system using an intracranial EEG epilepsy database with annotated clinical and subclinical seizure events. Patients were selected based on a postoperative outcome of Engel class I, indicating that intracranial electrodes were positioned at an informative location. After the first 24 hours of neural recordings are accumulated, feature extraction is performed by the system to generate an initial training set. Labelled subclinical and clinical seizure events, as labelled by an expert in the field, are removed along with a surrounding period of recordings, in this case 10 minutes of surrounding period. An OC-SVM model is trained and stored on an FPGA fabric along with feature normalization coefficients used for the training data. In this case, generally, minimizing misclassification of normal physiological neural activity while ensuring that pathological activity is captured is a key consideration. To enable this trade-off, classifier output is smoothed using a moving average window, which can be increased at the expense of detection latency. Once highlighted activity has been annotated, for example by the expert, a refined supervised model can be trained on a microserver to be uploaded to the implanted device. SVM training can then be performed on a computing system, for example, on a Zynq SoC's dual-core CPUs using a LibSVM implementation. The required training time generally scales linearly with the number of features used on the implanted device and the FPGA fabric. In this case, the number of training vectors were generally constrained by external memory to 50,000 with a dimensionality of 400. In some cases, incremental training can be performed to enable the use of larger volumes of data.

In this example, performance of the system was validated using 500 hours of iEEG data across four subjects in the expert-labelled epilepsy database. A combination of 16 depth and surface electrodes were determined on a per patient basis based on proximity to the seizure onset zone. The feature extraction implementation used five spectral bands per channel, each with a decay coefficients of 4, 6, 8, 10, 12, 14 and 16. The resulting feature vector had a dimensionality of 560. An illustration of the feature space for an electrode placed in the seizure onset zone and the resulting OC-SVM output are shown in FIG. 6; where detected outlier activity corresponds to an expert labelled clinical seizure onset time segment. In this experiment, using the system, a seizure detection rate of 97.05% was achieved.

Although the foregoing embodiments generally describe a support vector machine (SVM) for the machine learning model, any suitable machine learning model or technique can be used; for example, artificial neural networks (ANNs), Logistic Regression, Nearest Neighbors classifiers, or the like.

Although the foregoing has been described with reference to certain specific embodiments, various modifications thereto will be apparent to those skilled in the art without departing from the spirit and scope of the invention as outlined in the appended claims. The entire disclosures of all references recited above are incorporated herein by reference.

The invention claimed is:

1. A computer-implemented method for classifying time series data for identification of a state, the time series data comprises neural physiological signals and the state comprises a neural physiological event, the time series data comprising a series of samples, the method comprising:
   training a machine learning model to classify occurrences of the state by classifying a representative feature vector, using a respective training set, the respective training set comprising feature vectors of the time series data labelled with occurrences of the state;
   receiving a new time series data stream;
   determining whether a current sample in the new time series data stream is an occurrence of the state by determining a classified feature vector, the classified feature vector determined by passing the current sample and samples in at least one continuous sampling window into the trained machine learning model, each continuous sampling window comprising one or more preceding samples from the time series data, an epoch for each respective continuous sampling window determined according to a respective exponential decay rate; and
   outputting the determination of whether the current sample is an occurrence of the state.

2. The method of claim 1, wherein each continuous sampling window is recursively defined based on the epoch of a previous iteration of the respective window subtracted by the respective decay rate multiplied by the epoch of such previous iteration.

3. The method of claim 2, wherein the at least one continuous sampling window comprises at least two continuous sampling windows, the epoch of each of the continuous sampling windows being defined by a different exponential decay rate.

4. The method of claim 3, wherein each exponential decay rate is a reciprocal of a power of 2.

5. The method of claim 4, where each exponential decay rate is in a range of $1/2$ to $1/(2^{16})$.

6. The method of claim 3, wherein each epoch is on an order of minutes or less.

7. The method of claim 3, wherein the machine learning model uses one of linear, polynomial and radial-basis function (RBF) kernels.

8. The method of claim 3, wherein the time series data comprises electroencephalography (EEG) signals and the state comprises one or more onset biomarkers associated with a seizure.

9. The method of claim 2, wherein the at least one continuous sampling window comprises a plurality of continuous sampling windows organized into at least two banks of continuous sampling windows, each bank comprising at least one continuous sampling window, the continuous sampling windows in each bank having a different exponential decay rate than the continuous sampling windows in the other banks.

10. A system for classifying time series data for identification of a state, the system comprising one or more processors and one or more memory units, the time series data comprises neural physiological signals and the state comprises a neural physiological event, the one or more memory units storing the time series data comprising a series of samples, the one or more processors in communication with the one or more memory units and configured to execute:
   a training module for training a machine learning model to classify occurrences of the state by classifying a representative feature vector, using a respective training set, the respective training set comprising feature vectors of the time series data labelled with occurrences of the state;
   an input module for receiving a new time series data stream comprising a plurality of samples;
   an exponential decay module for defining at least one continuous sampling window, each continuous sampling window comprising one or more samples from the time series data preceding a current sample, an epoch for each respective continuous sampling window determined according to a respective exponential decay rate;

a support vector module for determining whether a current sample in the new time series data stream is an occurrence of the state by determining a classified feature vector, the classified feature vector determined by passing the current sample and samples in the at least one continuous sampling window into the trained machine learning model; and an output module for outputting the determination of whether the current sample is an occurrence of the state.

11. The system of claim 10, wherein each continuous sampling window is recursively defined based on the epoch of a previous iteration of the respective window subtracted by the respective decay rate multiplied by the epoch of such previous iteration.

12. The system of claim 11, wherein the at least one continuous sampling window comprises at least two continuous sampling windows, the epoch of each of the continuous sampling windows being defined by a different exponential decay rate.

13. The system of claim 12, wherein each exponential decay rate is a reciprocal of a power of 2.

14. The system of claim 13, where each exponential decay rate is in a range of ½ to $1/(2^{16})$.

15. The system of claim 12, wherein each epoch is on an order of minutes or less.

16. The system of claim 12, wherein the machine learning model uses one of linear, polynomial and radial-basis function (RBF) kernels.

17. The system of claim 12, wherein the time series data comprises electroencephalography (EEG) signals captured by electrodes in communication with the system, and the state comprises one or more onset biomarkers associated with a seizure.

18. The system of claim 11, wherein the exponential decay module defines a plurality of continuous sampling windows organized into at least two banks of continuous sampling windows, each bank comprising at least one continuous sampling window, the continuous sampling windows in each bank having a different exponential decay rate than the continuous sampling windows in the other banks.

* * * * *